United States Patent [19]

Samsoondar

[11] Patent Number: 5,939,327

[45] Date of Patent: Aug. 17, 1999

[54] MEASUREMENT OF BILE PIGMENTS IN SERUM OR PLASMA

[75] Inventor: James Samsoondar, Missisauga, Canada

[73] Assignee: CME Telemetrix, Inc., Canada

[21] Appl. No.: 08/862,391

[22] Filed: May 23, 1997

[30] Foreign Application Priority Data

May 24, 1996 [GB] United Kingdom .................... 9611011

[51] Int. Cl.$^6$ .................................................... G01N 33/00
[52] U.S. Cl. .............................. 436/97; 436/164; 702/19
[58] Field of Search .................................. 436/8, 12, 97, 436/164; 702/19

[56] References Cited

U.S. PATENT DOCUMENTS

| | | |
|---|---|---|
| 3,477,818 | 11/1969 | Fried et al. |
| 4,839,279 | 6/1989 | Kosaka et al. ............................ 435/25 |
| 4,985,360 | 1/1991 | Takahashi ............................ 435/25 X |
| 5,262,304 | 11/1993 | Taniguchi .................................. 435/25 |
| 5,278,073 | 1/1994 | Grandjean ................................. 436/12 |

FOREIGN PATENT DOCUMENTS

| | | |
|---|---|---|
| 2018166 | 4/1990 | Canada . |
| 2109896 | 11/1993 | Canada . |
| 2019511 | 9/1994 | Canada . |

*Primary Examiner*—Maureen M. Wallenhorst
*Attorney, Agent, or Firm*—Fitzpatrick, Cella, Harper & Scinto

[57] ABSTRACT

A method which provides a quick simple means of assessing plasma or serum specimen integrity with respect to bile pigments is described. Application of the method simultaneously screens serum or plasma specimens for elevated levels of bilirubin (BR) and biliverdin (BV) by providing a measure of these interferents known as the bilirubin-biliverdin index or BBI. The method involves determination of concentrations of BV in a plasma or serum specimen, based on the results of spectrophotometric determinations of absorbance or reflectance measurements conducted in the near infrared region, and thereby a determination of the BBI in respect of the specimen and on the basis of the resulting BBI a decision as to acceptance or rejection of the sample.

9 Claims, 5 Drawing Sheets

MEASUREMENT OF BILE PIGMENTS IN SERUM OR PLASMA

FIELD OF INVENTION

This invention relates to spectrometry and spectrophotometric analysis of blood samples. In particular, this invention relates to a method for providing a non-destructive pre-test screen of specimen integrity with respect to bile pigments in serum or plasma, referred to as the Bilirubin-Biliverdin-Index (BBI), by measurement of absorbance or reflectance. The BBI is a combined measurement of bilirubin (BR) and biliverdin (BV).

BACKGROUND OF INVENTION

Clinical laboratory tests are routinely performed on the serum or plasma of whole blood. In a routine assay, red blood cells are separated from plasma by centrifugation, of red blood cells and various plasma proteins are separated from serum by clotting prior to centrifugation. Hemoglobin, BR and light-scattering substances like lipid particles are typical substances which will interfere with, and affect spectrophotometric and other blood analytical measurements. Such substances are referred to as interferents and their concentrations may be determined by measurement of absorption of different wavelengths of light in serum or plasma specimens which measurements are then compared with values obtained through calibration using reference measurements for the interferent of interest in serum or plasma specimens. BR concentration is determined by measurement of absorption of different wavelengths of light in serum or plasma specimens which are then compared with values obtained through calibration using reference measurements for BR in serum or plasma specimens. On the basis of the results from measurements of one interferent at a time, or any two or more interferents at a time, in comparison with reference measurements of various levels of interferents, a decision is made concerning whether to reject or accept the sample for further testing.

Elevated BR can be due to disease states, hyperlipidemia can be due to disease states and dietary conditions, and hemoglobinemia can be due to disease states and as a result of specimen handling. Clinical laboratories currently emphasize these three potential interferents. Biliverdin, (BV), a fourth potential interferent, is not often mentioned.

Upon visual inspection, BR gives a yellow or orange color to serum and plasma, and is recognized as the major bile pigment in serum or plasma. Specimens which appear greenish in color are usually classified as hyperbilirubinemic, but it is likely that BV is responsible for the greenish color, and these specimens may, nevertheless, have acceptable levels of BR. A yellow color chart is available for visual grading of BR levels in serum or plasma, but there is no known color chart for green bile pigment. Visual inspection may still provide an opportunity for rejection of green specimens, however, for automated systems, no method exists for screening serum or plasma specimens for hyperbiliverdinemia.

SUMMARY OF INVENTION

The disadvantages of the prior art which measures bilirubin as the bile pigment interferent may be overcome by providing a method which simultaneously screens serum or plasma specimens for elevated levels of BR and BV. This is achieved by the present invention by providing a measure of these interferents known as the BBI. In its broad aspect the present invention provides a method for determining serum and plasma specimen integrity with respect to bile pigments.

In another aspect, the present invention provides a quick and simple means of simultaneously evaluating concentrations of BR and BV, based on the results of spectrophotometric determinations of absorbance or reflectance measurements conducted in the near infrared region.

In another aspect, the present invention provides a quick and simple means of simultaneously evaluating concentrations of BR and BV, based on the results of spectrophotometric determinations of absorbance or reflectance measurements conducted in the near infrared region and thereby allowing for a decision to be made as to whether to reject or retain a specimen for further testing.

In another aspect of the invention, a method for providing the concentration of BV in a specimen is provided and thereby allowing for a decision to be made as to whether to reject or retain a specimen for further testing. In this respect there is provided an algorithm for measuring BV concentration based on the results of spectrophotometric determinations of absorbance or reflectance measurements conducted in the near infrared region. This measurement is described for use in determining the BBI.

The method of the present invention can be used in conjunction with screening for hemolysis and turbidity and uses the same spectral data used for screening samples for hemolysis and turbidity, in assessing BR and BV.

DESCRIPTION OF THE INVENTION

The absorbance spectra of greenish specimens can be reproduced by spiking serum which appears normal, with biliverdin dihydrochloride. The characteristic absorbance peak from a green specimen and specimen spiked with 0.4 mg/dL biliverdin dihydrochloride, is maximum at 648 nm. The absorbance maximum shifts towards longer wavelengths as the BV concentration is increased. We hypothesize that the observed spectral shift is due to the dihydrochloride salt of BV which was used instead of BV, and nonlinear responses of absorbances with respect to biliverdin dihydrochloride concentration.

Figure 1:
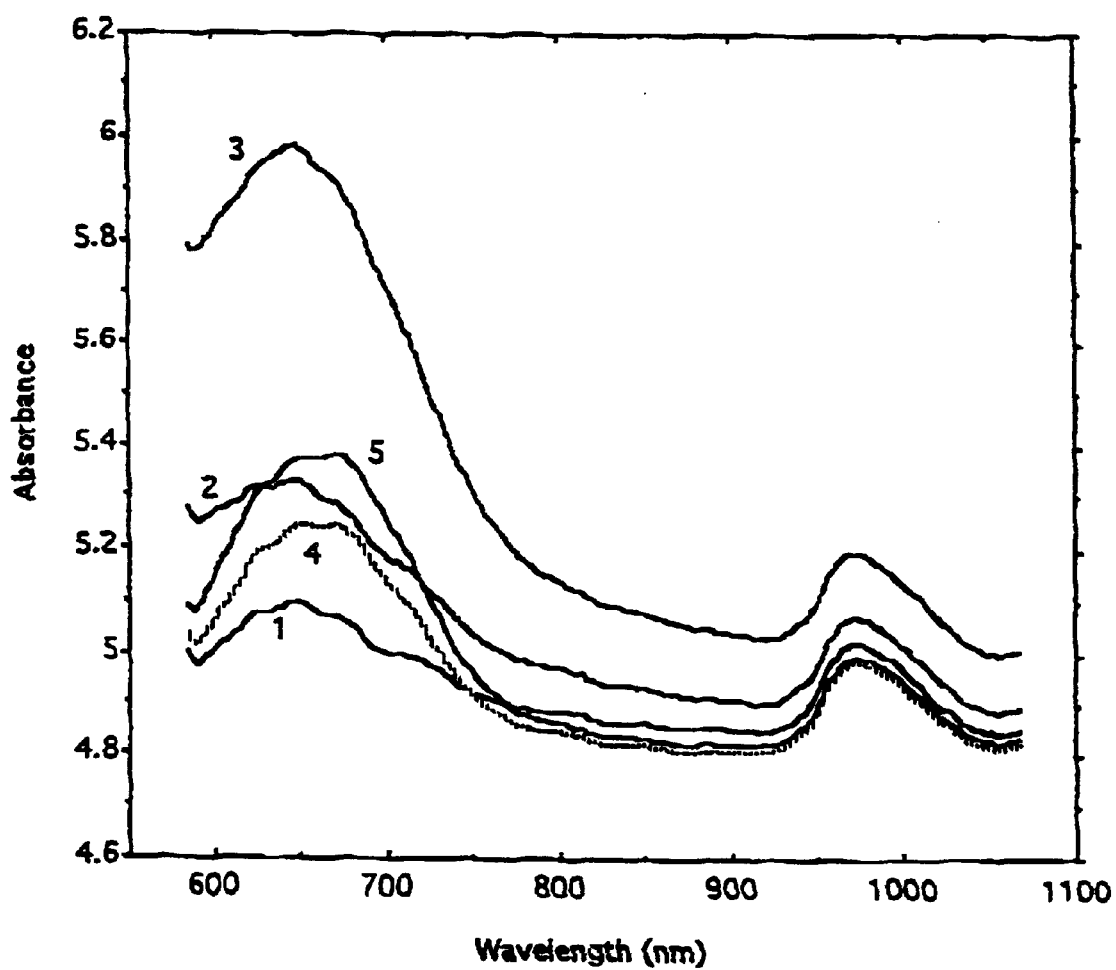
FIG. 1 is a graphic representation of the absorbance spectra of various specimens in labelled translucent plastic tubes.

Referring now to FIG. 1, shown is an example of a serum specimen which appears normal (#1), a yellow serum specimen with total BR of 350 umol/L (#2) and a green serum specimen with total BR of 327 umol/L and some turbidity (#3); spectra #4 and #5 are the spectra of serum specimens spiked with 0.8 and 1.2 mg/dL BV respectively, which appeared normal before the BV was added. The intense absorbance at 648 nm is present in the green serum specimen, but absent in the yellow serum specimen. On this basis it is hypothesized that the green pigment is BV. All determinations as to normal, yellow or green appearance of the specimens were made on the basis of visual inspection.

BV is the precursor of BR, and if BR becomes oxidized, it will revert to BV. BV is not present in normal serum, but regularly accompanies BR in the serum of patients with carcinomatous obstruction of the bile duct, and frequently in that of patients with liver cirrhosis, and bile duct occlusion of gallstones.

An instrument for use in measuring interferents on the basis of measurements of absorbance or reflection of near infrared radiation, was calibrated for BV as follows:

Twenty different serum specimens, which, on a visual inspection basis appeared normal, were spiked with biliverdin dihydrochloride (dissolved initially in 50% methanol-50% water and diluted further with water). The specimens were placed in different labelled tubes, and their absorbance spectra recorded, after the light was transmitted through the labels, tube walls and specimens. Hemoglobin prepared by removing the clear plasma, which appeared normal, from centrifuged whole blood, and lysing the red blood cells with an equal volume of lysing buffer. The hemoglobin content of the lysate was measured on a Coulter-STKS™. The 20 specimens were further spiked with the Hb and the absorbance spectra re-recorded and stored. On a second day, 23 new serum specimens, which appeared normal, were spiked as before with BV, and after their absorbance spectra re-recorded and stored. These 86 spectra which contained up to 4 mg/dL BV, up to 6.6 g/L Hb, and up to 7.3 g/L IL were analyzed by a statistical computer program and an algorithm was developed for BV.

Figure 2:
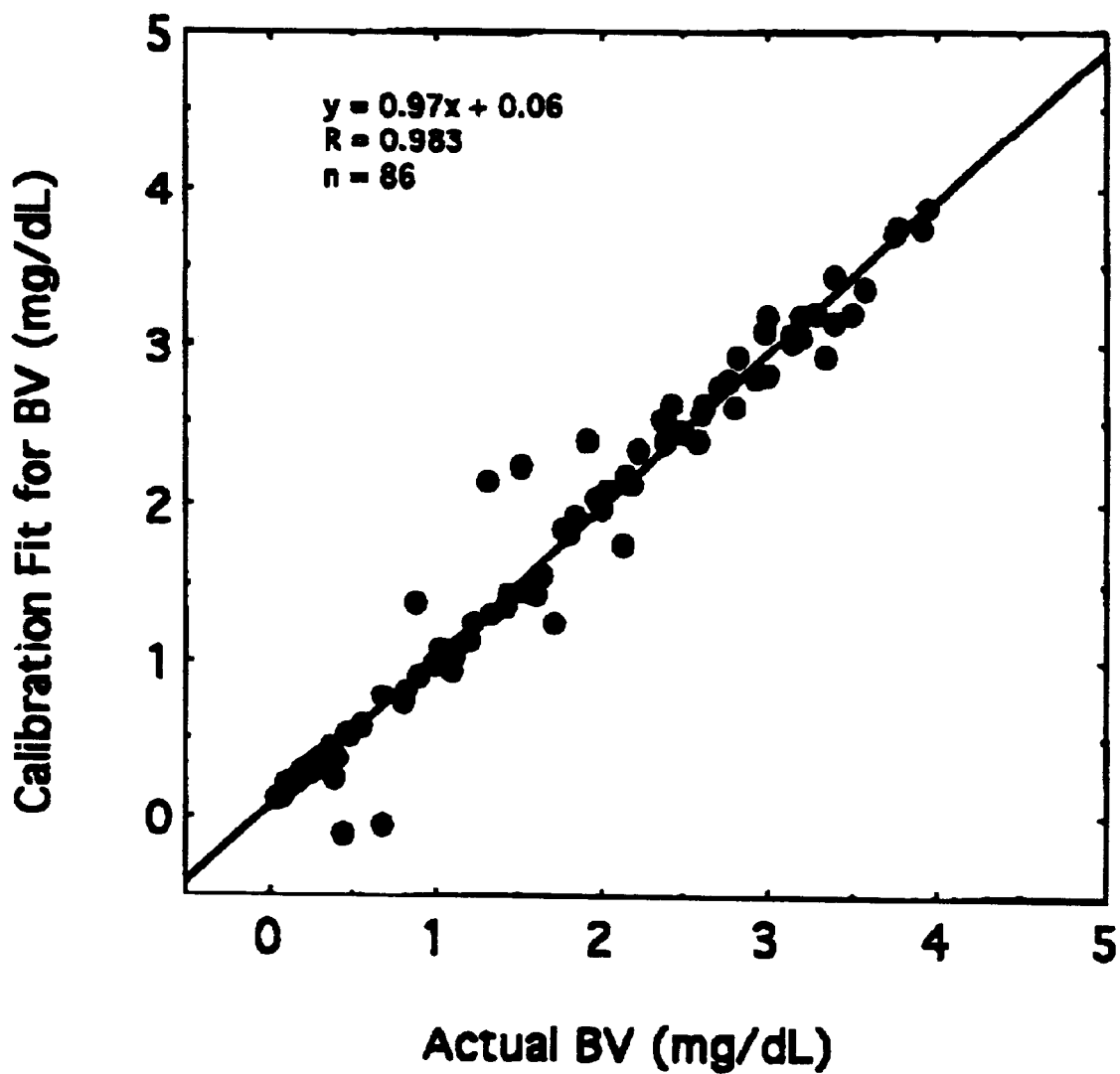
FIG. 2 is a graphic representation of the results of a linear regression fit of data for BV calibration in units of miligrams per deciliter on the abscissa and ordinant axes.

Referring to FIG. 2, this Figure is a graphic representation of the results of a linear regression fit of the data generated from the BV calibration. The algorithm which was developed for BV based on this data is as follows:

mg/dL BV=40.97 (692 nm)−81.52 (918 nm)−46.70 (969 nm)−0.85 where the (X nm) is the first derivative of the absorbance at the wavelength specified.

BBI=mg/dL×4 (rounded upwards to the nearest whole number)

While the number 4 has been chosen as the constant to provide the BBI, any constant can be used which provides a range of BBI for determination. An acceptable range which includes most specimens is 0–10. With this calibration and the algorithm, the present invention may be used for detecting and quantifying BV, for the purposes of rapidly pre-screening plasma and/or serum specimens which will be further analyzed, or in any setting currently employing a visual determination of the level of bile pigments in serum/plasma. It may also be used on a retrospective basis where there is a disagreement between test results and the clinical status of a patient. The algorithm may be used instead of any algorithms developed for bilirubin through the use of similar instrumentation.

Figure 3:
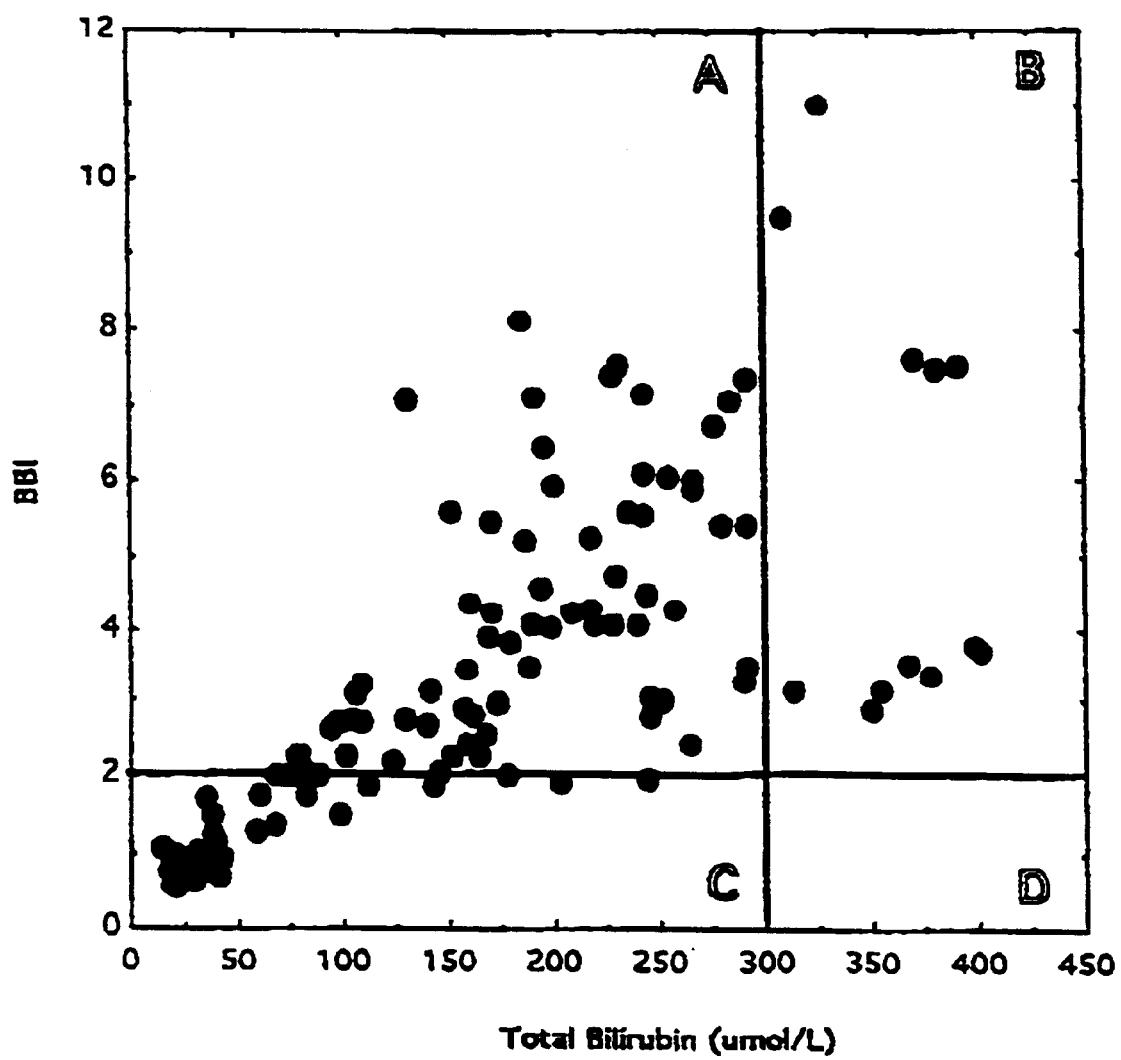
FIG. 3 is a scatterplot for 120 icteric serum specimens, with the abscissa in units of micromoles per liter total BR as measured on the Kodak Ektachem™, and with the ordinant axis in BBI units.
Figure 4:
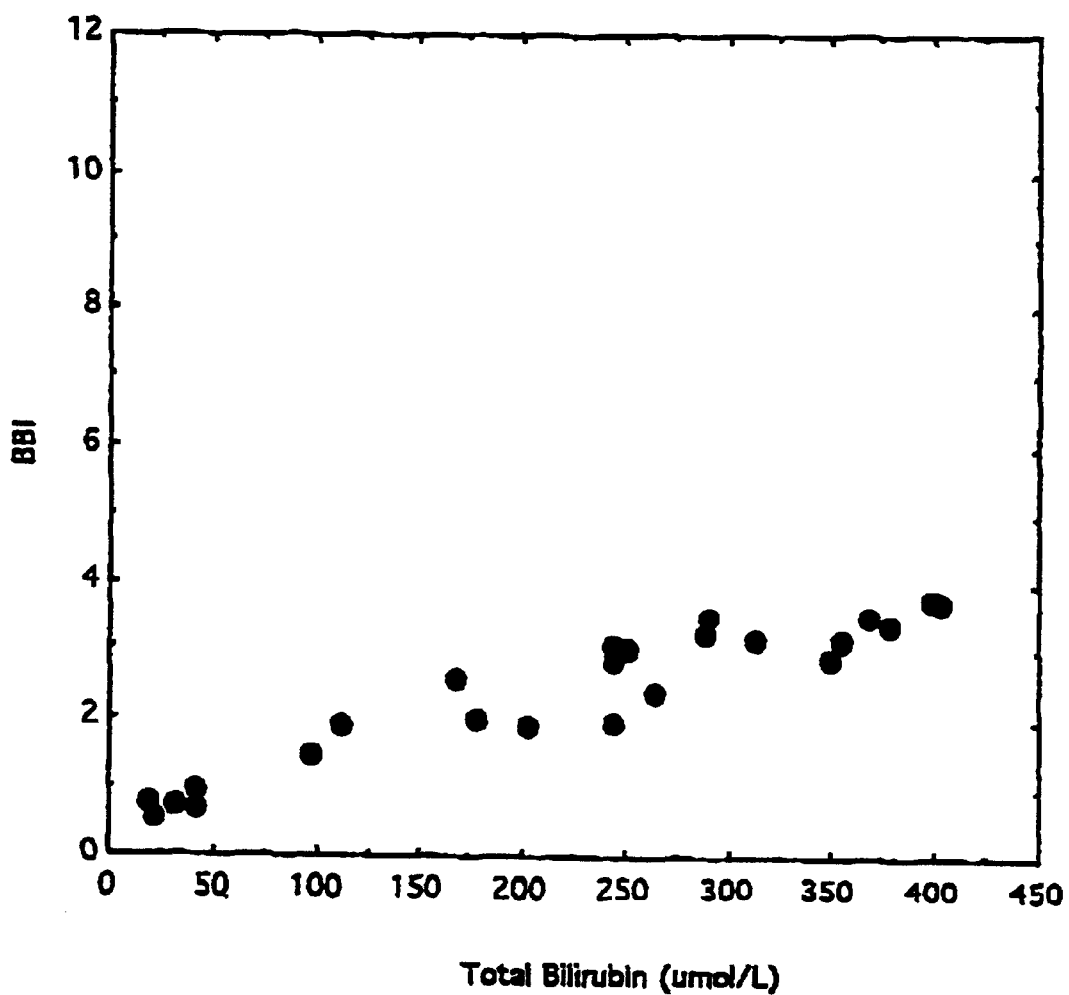
FIG. 4 is the same as FIG. 3 with 25 of the 120 serum specimens which originated from a liver transplant center, and the specimens contained different amounts of yellow or orange pigment.
Figure 5:
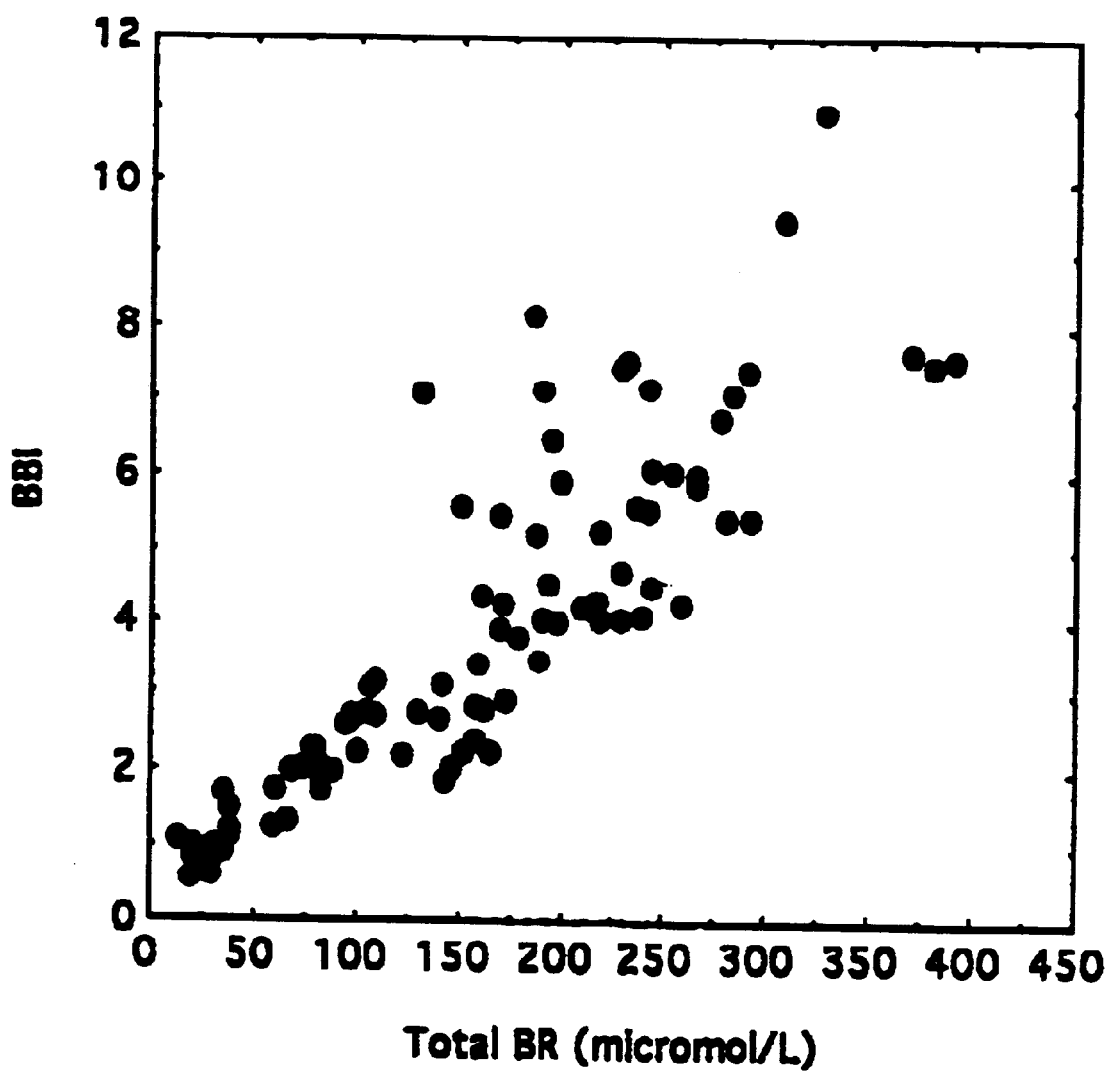
FIG. 5 is the same as FIG. 3 with 95 of the 120 serum specimens which originated from two different hospitals which did not perform liver transplant, and the specimens contained different amounts of green pigment.

The absorbance spectra for 120 different icteric serum specimens were stored and used with the BBI algorithm to predict the BBI for each specimen. The total bilirubin concentration in each specimen was determined on a Kodak Ektachem™, and a scatterplot of the two sets of results are presented in FIG. 3, with umol/L total bilirubin on the abscissa, and the BBI on the ordinate. To clearly explain how BBI measures both BR and BV, when the algorithm used a calibration for BV only, the 120 specimens were divided into 2 sets:

The first set includes 25 specimens collected from a liver transplant center, and these specimens appeared to contain yellow pigment, with no obvious green pigment. The scatter plot for these 25 are provided in FIG. 4 with the axes set at the same scale as described for FIG. 3. The remaining 95 specimens were collected from 2 different hospitals which do not perform liver transplants. These specimens appeared to contain various amounts of green pigment. The scatter plot for these 95 are given in FIG. 5 with the axes set at the same scale as described for FIGS. 3 and 4. It may be observed from FIG. 4 that there is a proportionality between the predicted BBI and the total BR. In FIG. 5 a proportionality between the predicted BBI and the total BR is also observed but the constant of proportionality is relatively larger; also there are several specimens which showed a disproportionate increase in BBI over the total BR. Referring again to the combined data set illustrated in FIG. 3, specimens may be rejected for containing too much bile pigment based on a BBI cut-off (sections A & B), or rejected based on a total BR cut-off (sections B & D). If the total BR cut-off is used as a specimen rejection criterion, only specimens in section B will be rejected (no specimen appeared in section D): if the BBI cut-off is used as a specimen rejection criterion, specimens in both sections A and B will be rejected. As may be seen from FIG. 3 the BBI cut off value is 2, however it can be 3 depending upon the rejection rate tolerated by the laboratory using this method. Also, it follows that another appropriate range (as opposed to 0–10) may be employed with a different numerical cut off value. Regardless, the cut off value chosen should be that which provides a tolerable rejection rate for specimens. Therefore by using the BBI cut-off, specimens will be rejected due to elevated levels of total bilirubin (section B), and also due to elevated BBI (section A); if visual inspection is employed, specimens in section A will be rejected due to their greenish appearance. All specimens with normal levels of bile pigments should appear in section C; 58 serum specimens with variable amounts of hemolysis and lipemia but no bile pigments by visual observation, all had predicted BBI's of zero.

While the invention has been particularly shown and described with reference to preferred embodiments, it will be understood by those skilled in the art that various other changes in form and detail may be made without departing from the spirit and scope of the invention.

I claim:

1. A method for determining, in a primary container, specimen integrity with respect to bile pigment content comprising the following steps:

a. development of a calibration algorithm for biliverdin (BV) on an instrument which is used for measuring bile pigment interferents including bilirubin and biliverdin on the basis of absorbance or reflectance of radiation;

b. measuring absorbance or reflectance of radiation by a specimen in a primary container with said instrument;

c. obtaining a bilirubin-biliverdin index (BBI) value for said specimen by conducting the following steps:

i. determining bilirubin concentration in said specimen from said absorbance or reflectance measurement;

ii. determining biliverdin (BV) concentration in said specimen by incorporating said absorbance or reflectance measurement into said algorithm; and iii. multiplying said biliverdin (BV) concentration by a factor;

d. comparing said BBI value with a predetermined BBI cutoff value; and e. rejecting or accepting said specimen based on said comparison.

2. The method of claim 1 wherein said measurement is conducted with radiation in the near-infrared region.

3. The method of claim 1 wherein said specimen in a primary container is serum in a laboratory test tube.

4. The method of claim 1 wherein said specimen in a primary container is plasma contained in a laboratory test tube.

5. The method of claim 1 wherein absorbance of said radiation is measured.

6. The method of claim 1 wherein said calibration algorithm is developed with plasma specimens spiked with biliverdin dihydrochloride.

7. The method of claim 1 wherein said factor is 4 and said BBI cut off value is 2.

8. A method for determining, in a primary container, plasma or serum specimen integrity with respect to bile pigment content comprising the following steps:

a. development of a calibration algorithm for biliverdin (BV) on a spectrophotometer on the basis of absorbance of near-infrared radiation by normal plasma or serum specimens spiked with biliverdin dihydrochloride;

b. measuring absorbance of radiation by a specimen in a primary container using said spectrophotometer;

d. obtaining a bilirubin-biliverdin index (BBI) value for said specimen by conducting the following steps:
  i. determining bilirubin concentration in said specimen from said absorbance measurement;
  ii. determining biliverdin (BV) concentration in said specimen by incorporating said absorbance measurement into said algorithm; and
  iii. multiplying said biliverdin (BV) concentration by a factor of 4;

e. comparing said BBI value with a predetermined BBI cutoff value of 2; and f. rejecting said specimen if said BBI value exceeds said BBI cutoff value or accepting said specimen if said BBI value is less than said BBI cutoff value.

9. The method of claim 8 wherein said algorithm is:

mg/dL biliverdin (BV)=40.97 (692 nm)−81.52 (918 nm)−46.70 (969 nm)−0.85 wherein (X nm) is a first derivative of the absorbance at the wavelength specified.

* * * * *